United States Patent [19]

Fischer

[11] Patent Number: 5,371,297
[45] Date of Patent: Dec. 6, 1994

[54] PREPARATION OF ALDEHYDES

[75] Inventor: Rolf Fischer, Heidelberg, Germany

[73] Assignee: BASF Aktiengesellschaft, Ludwigshafen, Germany

[21] Appl. No.: 121,440

[22] Filed: Sep. 16, 1993

[30] Foreign Application Priority Data

Sep. 21, 1992 [DE] Germany .................... 4231490

[51] Int. Cl.$^5$ .................................... C07C 45/54
[52] U.S. Cl. .................................... 568/465; 568/449; 568/458
[58] Field of Search ............... 568/449, 465, 458

[56] References Cited

U.S. PATENT DOCUMENTS

| | | | |
|---|---|---|---|
| 3,721,714 | 3/1973 | Fenton | 568/449 |
| 4,417,073 | 11/1983 | Ackermann et al. | 560/105 |
| 4,804,776 | 2/1989 | Baudin et al. | 560/51 |
| 4,866,210 | 9/1989 | Hoelderich et al. | 568/392 |

FOREIGN PATENT DOCUMENTS

2573070 5/1986 France .................... 568/449
3045102 9/1969 Germany .

OTHER PUBLICATIONS

Decarbalkoxylation of B–Keto Esters..., Greens et al. Tetrahedron Ltrs. No. 31, pp. 2707–2708, 1976, Pergamon Press.

Houben–Weyl, Methoden der organischen Chemie, Ed. IV (1952) vol. 8, pp. 600–612.

*Primary Examiner*—Werren B. Lone
*Attorney, Agent, or Firm*—Keil & Weinkauf

[57] ABSTRACT

A process for the preparation of aldehydes of the general formula I

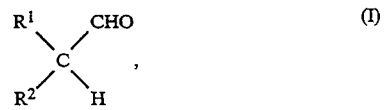
(I)

in which
  R$^1$, R$^2$ denote hydrogen, C$_1$–C$_{12}$ alkyl, C$_3$–C$_8$ cycloalkyl, acyl, aryl, or C$_7$–C$_{20}$ aralkyl or together stand for —(CH$_2$)$_n$—X—(CH$_2$)$_m$—,
  X denotes methylene, oxygen, sulfur, NH or NR$_3$ and n, m stand for an integer from 0 bis 8, wherein a geminal formyl ester of the general formula II

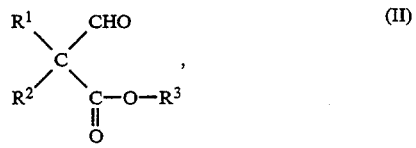
(II)

in which R$^1$ and R$^2$ have the aforementioned meanings and R$^3$ denotes C$_1$–C$_{12}$ alkyl, is caused to react in the presence of an acid catalyst at temperatures ranging from 150° to 400° C.

8 Claims, No Drawings

PREPARATION OF ALDEHYDES

The present invention relates to a process for the preparation of aldehydes by the causing geminal formyl esters to react in the presence of acid catalysts at elevated temperatures.

DE-AW 3,045,102 describes a process for the preparation of substituted acetic acids, their esters or acetonitriles by the reaction of malonates or cyanates at elevated temperatures in the presence of catalysts.

Houben-Weyl, Methoden der organischen Chemie, Edition IV (1952), Vol. 8, pp. 600 to 612 discloses that it is possible to prepare substituted geminal cyanates, eg, by alkylation or acylation of cyanates. These can be converted to nitriles following acid or alkaline hydrolysis of the ester group by the elimination of the carboxylic acid group. Such reactions are generally associated with salt production.

It is thus an object of the present invention to overcome the aforementioned drawbacks.

Accordingly, we have found a novel and improved process for the manufacture of aldehydes of the general formula I

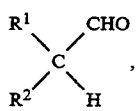

in which
$R^1$, $R^2$ denote hydrogen, $C_1$–$C_{12}$ alkyl, $C_3$–$C_8$ cycloalkyl, acyl, aryl, or $C_7$–$C_{20}$ aralkyl or together stand for —$(CH_2)_n$—X—$(CH_2)_m$—,
X denotes methylene, oxygen, sulfur, NH or $NR_3$ and n, m stand for an integer from 0 bis 8,
wherein a geminal formyl ester of the general formula II

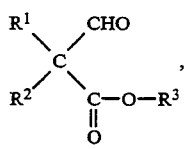

in which $R^1$ and $R^2$ have the aforementioned meanings and $R^3$ denotes $C_1$–$C_{12}$ alkyl, is caused to react in the presence of an acid catalyst at temperatures ranging from 150° to 400° C.

The process of the invention can be carried out as follows:

The geminal formyl esters II are converted to the aldehydes I at elevated temperatures by reaction in contact with acid catalysts.

The reaction can be carried out continuously or batchwise at temperatures ranging from 150° to 400° C. and preferably from 170° to 400° C. and more preferably from 200° to 300° C. The pressure used for the reaction is not crucial. It is advantageous to use pressures ranging from 0.1 to 100 bar and especially from 1 to 10 bar. The convertion of the geminal formyl esters II to aldehydes I can take place in the liquid phase or preferably in the gas phase. It is advantageous to carry out the process using a throughput of from 0.1 to 10 g and especially from 0.1 to 5 g of compound II per gram of catalyst per hour.

The reaction herein proposed may be carried out in the absence of solvents. It may be advantageous, however, to operate in the presence of solvents. Suitable solvents that may be used are, for example, ethers such as diethylether, tetrahydrofuran, and dioxan, aromatics such as benzene, toluene, and the xylenes, chlorinated hydrocarbons such as chloroform and methylene chloride and preferably alcohols such as for example $C_1$–$C_8$ alcohols, in particular $C_1$–$C_5$ alcohols such as methanol, ethanol, n-propanol, isopropanol, butanols, and pentanols. The concentration of the solvent is usually from 5 to 90 wt % based on compound II used.

The reaction can be carried out continuously or batchwise as a fixed bed reaction using a fixed bed catalyst, for example by a technique using packed bubble-cap columns or trickle-bed columns in the liquid phase or in the gas phase, eg, in a fluid bed or alternatively using a fixed bed catalyst suspended in the liquid phase.

The reaction of the geminal formyl esters II in the liquid phase is carried out for example by heating a mixture of compound II and optionally a solvent to the desired reaction temperature in the presence of a suspended fixed bed catalyst. Following completion of the reaction the reaction mixture is cooled, and the catalyst is isolated, eg, by filtration or neutralization.

The reaction mixture can then be fractionally distilled for the purpose of isolating the desired aldehyde I.

In a preferred embodiment of the process of the invention, carried out in the gas phase over a fixed bed or fluidized catalyst and in the presence of an alcohol, the following procedure can be adopted, for example:

A mixture of compound II and the respective alcohol is vaporized and then, optionally together with an inert gas such as nitrogen, carbon dioxide or argon, passed at the desired reaction temperature as gas over a fixed bed catalyst or a fluid catalyst, the latter being maintained in rising and falling turbulence. The effluent is condensed by means of suitable cooling means and then purified by fractional distillation. The desired compound I is separated. Unconverted compound II can be recycled to the reaction if desired.

Basically, diverse acid catalysts such as mineral acids, sulfonic acids, carboxylic acids and Lewis acids are suitable. Particularly suitable acid catalysts are metal oxides of Group Ia to Group Va elements and Group Ib to VIIIb elements as well as oxides of the lanthanides. Examples of such metal oxides are boron trioxide, aluminum oxide, silicon dioxide, titanium dioxide, zinc oxide, niobium oxide, vanadium pentoxide, molybdenum oxide, cerium oxide and tungstic oxide and preferably aluminum oxide, silicon dioxide, titanium dioxide, zirconium dioxide, boron trioxide, vanadium pentoxide, molybdenum oxide, tungstic oxide and mixtures thereof. Aluminum oxide is particularly preferred.

Other suitable acid catalysts are acid phosphates, acid ion exchangers, silicates and zeolites such as for example zeolites of the mordenite group, X-type, Y-type or L-type zeolites such as mordenite, erionite and faujasite, zeolites having a pentasil structure such as ZSM-5, ZSM-11, and ZBM-10 zeolites are preferred, more preferably ZSM-5 and ZSM-11 zeolites.

Other suitable acid catalysts are hetero poly acids such as $H_3[PW_{12}O_{40}]$, $H_3[PMo_{12}O_{40}]$, or $H_4[SiW_{12}O_{40}]$ and preferably $H_3[PW_{12}O_{40}]$ and $H_3[PW_{12}O_{40}]$ and $H_3[PMo_{12}O_{40}]$ and more preferably $H_3[PW_{12}O_{40}]$.

The link X, the substituents $R^1$, $R^2$, $R^3$ and the indices n and m in the compounds I and II have the following meanings:

$R^1$, $R^2$ independently denote hydrogen, $C_1$–$C_{12}$ alkyl such as methyl, ethyl, n-propyl, isopropyl, n-butyl, isobutyl, sec-butyl, tert-butyl, n-pentyl, isopentyl, sec-pentyl, neo-pentyl, 1,2-Dimethylpropyl, n-hexyl, isohexyl, sex-hexyl, n-heptyl, isoheptyl, n-octyl, isooctyl, n-nonyl, isononyl, n-decyl, isodecyl, n-undecyl, isoundecyl, n-dodecyl, and isododecyl, and preferably $C_1$–$C_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec.-hexyl, n-heptyl, isoheptyl, n-octyl, and isooctyl, and more preferably $C_1$–$C_4$ alkyl such as methyl, ethyl, n-propyl, isopropyl, n-butyl, isobutyl, sec-butyl, and tert-butyl, $C_3$–$C_8$ cycloalkyl such as cyclopropyl, cyclobutyl, cyclopentyl, cyclohexyl, cycloheptyl, and cyclooctyl, and preferably cyclopentyl, cyclohexyl, and cyclooctyl, acyl such as actyl, aryl such as phenyl, 1-naphthyl, 2-naphthyl, 1-anthryl, 2-anthryl, and 9-anthryl, and preferably phenyl, 1-naphthyl, and 2-naphthyl, and more preferably phenyl, $C_7$–$C_{20}$ aralkyl and preferably $C_7$–$C_{12}$ phenylalkyl such as benzyl, 1-phenethyl, 2-phenethyl, 1-phenyl-propyl, 2-phenyl-propyl, 3-phenyl-propyl, 1-phenylbutyl, 2-phenyl-butyl, 3-phenylbutyl, and 4-phenyl-butyl, and more preferably benzyl, 1-phenethyl, and 2-phenethyl, —$(CH_2)_n$—X—$(CH_2)_m$—, X denotes methylene (—$CH_2$—), oxygen, sulfur,

NH, $NR^3$, $C_1$–$C_{12}$ alkyl such as methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl, and isododecryl, and preferably $C_1$–$C_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, iso-heptyl, n-octyl, and isooctyl, and more preferably $C_1$–$C_4$ alkyl such as methyl, ethyl, n-propyl, isopropyl, n-butyl, isobutyl, sec-butyl, and tert-butyl and n, m denote in each case an integer of from 0 to 8 such as 0, 1, 2, 3, 4, 5, 6, 7, and 8 and preferably an integer of from 1 to 4 such as 1, 2, 3, and 4.

Suitable geminal formyl esters of the formula II are, eg, methyl 2-formylvalerate and methyl 2-formylpropionate.

The compounds II required for the reaction of the present invention are generally known.

The aldehydes I which can be produced by the process of the invention are found to be valuable intermediates which are useful in many ways for organic syntheses.

EXAMPLES

The experiments were carried out by pumping solutions of the starting materials II in methanol continuously and at various temperatures to 5 g of γ aluminum oxide, which was situated in a stainless steel reactor spiral. The reactor was heated to the desired temperature in a hot-air furnace. A layer of inert material was placed upstream of the $Al_2O_3$ reactor bed, in which the added solution evaporated. The gaseous effluent was condensed, analyzed by gas chromatography, and purified by distillation if necessary.

EXAMPLE 1

59.6 g of a 20% strength solution of methyl 2-formylvalerate in methanol were fed to the reactor at a temperature of 200° C. over a period of 7.5 h. The combined effluent was distilled in a spinning band column. The distillate was found to contain 4.6 g of n-valeraldehyde (65% o, based on methyl 2-formylvalerate used).

EXAMPLE 2

42.5 g of a 20% strength solution of methyl 2-formyl-2-methylpropionate in methanol were fed over a period of 5 h to the reactor at a temperature of 200° C. The combined effluent was analyzed by gas chromatography (internal standard) giving an isobutyraldehyde yield of 29% (based on formyl ester used). In addition, 44% of unconverted formyl ester was found. The isobutyraldehyde selectivity is thus 52%.

We claim:

1. A process for the preparation of an aldehyde of the formula I

in which $R^1$, $R^2$ denote hydrogen, $C_1$–$C_{12}$alkyl, $C_3$–$C_8$ cycloalkyl, acyl, aryl, or $C_7$–$C_{20}$ar-alkyl or together stand for —$(CH_2)_n$—X—$(CH_2)_m$—, X denotes methylene, oxygen, sulfur, NH or $NR^3$ and n, m stand for an integer from 0 to 8, wherein a geminal formyl ester of the formula II

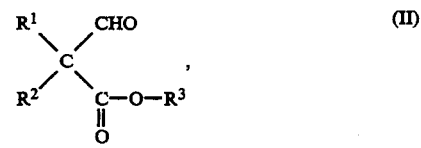

in which $R^1$ and $R^2$ have the aforementioned meanings and $R^3$ denotes $C_1$–$C_{12}$alkyl, is caused to react in the presence of an acid catalyst which is at least one catalyst selected from the group consisting of mineral acids, sulfonic acids, carboxylic acids, Lewis acids, metal oxides or Group Ia to Group Va elements and Group Ib to VIIIb, oxides of the lanthanides, acid phosphates, acid ion exchangers, silicates, zeolites and hetero poly acids at temperatures ranging from 150° to 400° C.

2. A process for the preparation of an aldehyde I as claimed in claim 1, wherein the acid catalyst is at least one member selected from the group consisting of a metal oxide of a Group Ia to Group Va element, of a Group Ib to Group VIIIb element, of an element in the lanthanide group in the Periodic Table of the Elements, a zeolite and hetero poly acide.

3. A process for the preparation of an aldehyde I as claimed in claim 1, wherein the acid catalyst is at least one member selected from the group consisting of aluminum oxide, silicon dioxide, titanium dioxide, zirconium dioxide, vanadium pentoxide, boron trioxide, an oxide of chromium, an oxide of molybdenum, and an oxide of tungsten.

4. A process for the preparation of an aldehyde I as claimed in claim 1, wherein the catalyst is a zeolite or hetero poly acid.

5. A process for the preparation of an aldehyde I as claimed in claim 1, wherein the catalyst is aluminum oxide.

6. A process for the preparation of an aldehyde I as claimed in claim 1, wherein the process is carried out in the presence of at least one solvent selected from the group consisting of diethylether, tetrahydrofuran, dioxan, benzene, toluene, chloroform, methylene chloride and $C_1$-$C_8$ alcohols.

7. A process for the preparation of an aldehyde I as claimed in claim 6, wherein the process is carried out in the presence of an alcohol.

8. A process for the preparation of an aldehyde I as claimed in claim 1, wherein the process is carried out in the gas phase.

* * * * *